United States Patent
Feltz et al.

[11] Patent Number: 5,864,148
[45] Date of Patent: *Jan. 26, 1999

[54] HIGH-TEMPERATURE GAS SENSOR

[75] Inventors: Adalbert Feltz; Friederike Lindner, both of Deutschlandsberg, Austria

[73] Assignee: Siemens Matsushita Components GmbH & Co. KG, Munich, Germany

[*] Notice: This patent issued on a continued prosecution application filed under 37 CFR 1.53(d), and is subject to the twenty year patent term provisions of 35 U.S.C. 154(a)(2).

[21] Appl. No.: 873,415

[22] Filed: Jun. 12, 1997

Related U.S. Application Data

[63] Continuation of Ser. No. 377,268, Jan. 24, 1995, abandoned.

[30] Foreign Application Priority Data

Jan. 25, 1994 [DE] Germany .......................... 44 02 117.8

[51] Int. Cl.$^6$ .................................................. H01L 29/12
[52] U.S. Cl. .............................. 257/43; 257/930; 338/34; 338/22 R; 422/94; 422/95
[58] Field of Search .............................. 257/43, 457, 703, 257/930; 73/23, 27 R; 338/34, 22 SD, 22 R; 422/94, 98, 95; 438/54, 55, 49, 382

[56] References Cited

U.S. PATENT DOCUMENTS

| | | | |
|---|---|---|---|
| 3,861,879 | 1/1975 | Taylor | 73/355 R |
| 4,362,765 | 12/1982 | Abe et al. | 427/535 |
| 4,507,643 | 3/1985 | Sunano et al. | 338/34 |
| 4,608,232 | 8/1986 | Sunano et al. | 73/23 |
| 5,071,828 | 12/1991 | Greuter et al. | 505/425 |
| 5,262,026 | 11/1993 | Nojima et al. | 204/491 |
| 5,423,973 | 6/1995 | Friese et al. | 204/426 |

FOREIGN PATENT DOCUMENTS

| | | |
|---|---|---|
| 30 28 249 | 2/1981 | Germany . |
| 30 40 243 | 6/1982 | Germany . |
| 29 33 971 | 12/1983 | Germany . |
| 33 22 534 A1 | 1/1985 | Germany . |
| 30 28 249 | 10/1985 | Germany . |
| 36 06 500 A1 | 9/1987 | Germany . |
| 37 43 399 | 7/1989 | Germany . |
| 37 43 399 A1 | 7/1989 | Germany . |
| 38 39 414 | 5/1990 | Germany . |
| 42 13 629 | 2/1994 | Germany . |
| 42 13 629 C1 | 2/1994 | Germany . |

OTHER PUBLICATIONS

Publ. Sensors and Actuators, B1 (1990), pp. 54–57, (Riegel et al.), "Analysis of Combustible Gases... ".
Publ. Trans. Faradey Soc. 62(1966), pp. 2566–2576, (Firth), Catalytic Oxidation of Methane on Palladium.
Publ. Measurement + Control, vol. 22, Jul./Aug. 1989, (Jones), pp. 176–182 "Trends in the development . . . ".

*Primary Examiner*—Minh Loan Tran
*Attorney, Agent, or Firm*—Herbert L. Lerner; Laurence A. Greenberg

[57] ABSTRACT

A high-temperature gas sensor for the detection of the heat tone of combustible gases includes a semiconducting ceramic layer with thermistor properties. The semiconducting ceramic layer is formed of an oxide ceramic semiconducting material having a defined crystalline structure and a thermistor characteristic of high sensitivity. A process for the manufacture of the high-temperature gas sensor includes sintering a loosely structured layer of powder particles of an oxide semiconductor with both a defined composition and high sinter activity for achieving a required high porosity of a semiconducting ceramic layer with thermistor properties.

6 Claims, 7 Drawing Sheets

HIGH-TEMPERATURE GAS SENSOR

This application is a continuation of application Ser. No. 08/377,268, filed on Jan. 24, 1995, now abandoned.

BACKGROUND OF THE INVENTION

1. Field of the Invention

The present invention relates to a high-temperature gas sensor for the detection of the heat tone of combustible gases in the form of a semiconducting ceramic layer with thermistor properties. The present invention also relates to a process for the manufacture of the high-temperature gas sensor.

Known technical solutions start with resistance thermometers based on noble metals, such as Pd-Au alloys, as is disclosed in the paper entitled: "Trans. Faraday Soc." 62 (1966) 2566, or coils of thin Pt wire, as is disclosed in the paper entitled: "Solid State Gas Sensors", IOP-Publ. Ltd, England 1987, which were proposed in U.K. Patent GB 892 530 for the control of combustion processes. The comparatively weak relationship between the electrical resistance of such metals and temperature is utilized so that the reaction heat released on the surface of a heated resistance wire as a consequence of catalytic oxidation of reducing gases serves as a temperature signal.

Applications at up to 800° C. have been suggested. Due to the relatively low sensitivity of only a few tenths of 1% change in resistance per degree on average, detection is severely and adversely affected by outside influences, such as the gas flow velocity. The detection range is thus restricted to approximately 0.1% of a combustible gas, as is reported in the paper entitled: "Measurement and Control" 22 (1989), 176. In order to increase the sensitivity and reduce the threshold temperature, German Published, Non-Prosecuted Application DE-OS 30 40 243 proposed the use of coatings with catalysts, such as aluminum oxide. The step to planar, integration-ready configurations for such gas sensors was documented in German Patent DE-PS 30 28 249.

Other technical solutions specify the use of a semiconducting component with a steep characteristic and therefore correspondingly greater sensitivity instead of the resistance wire. German Published, Non-Prosecuted Application DE-OS 38 39 414 A1 discloses that, in such a case, the temperature range is restricted to 200°–500° C., and German Published, Non-Prosecuted Application DE-OS 37 43 399 discloses that a passivating layer is required as an intermediate layer on the outside beneath the catalyst layer to protect the semiconductor. Metal oxide semiconductors, such as $SnO_2$, ZnO, $WO_3$ or $In_2O_3$ with an amorphous catalytic outer layer are described in German Patent DE-PS 29 33 971.

Another variant of proposed technical solutions for the detection of calorimetric signals with sufficient sensitivity relates to sensors which utilize the pyro-electric effect, such as is disclosed in the paper entitled: "Ferroelectrics" 54 (1984) 211 or in U.S. Pat. No. 3,861,879, or that utilize the steep temperature-resistance characteristic of a PTC thermistor ceramic, such as are disclosed in the paper entitled: "Sensors & Actuators", B1 (1990), 54. In the former case, application is limited by an upper temperature range, the ferroelectric phase conversion point, and is limited to the narrow temperature range of the ferroelectric phase conversion in the latter. The long-term stability of such materials under the application conditions are particularly problematic.

Due to the high-degree of non-linearity of the resistance-temperature characteristic, temperature measurement sensitivity in the range of a few percent change in resistance per degree as well as a high degree of stability and reproducibility of the measurement of a calorimetric signal can be expected with NTC thermistor sintered ceramics, such as is disclosed in German Published, Non-Prosecuted Application DE-OS 42 13 629 for non-aging thermistors, such as in the systems $Fe_xNi_yMn_{3-x-y}O_4$ and $Zn_zFe_{x-z}NiMn_{2-x}O_4$ (B constants 3400 to 4000 K), or as is disclosed in German Published, Non-Prosecuted Application DE-OS 42 13 629 for high-temperature applications up to 750° C., such as $MgNiMnO_4$ (B constant 4550 K), or as is disclosed in German Published, Non-Prosecuted Application DE-OS 43 27 285 for temperatures up to 1200° C., such as $Sr_7Mn_4O_{15}$ (B constant 10500 K).

SUMMARY OF THE INVENTION

It is accordingly an object of the invention to provide a high-temperature gas sensor for the detection of calorimetric signals with a high degree of stability and sensitivity for a temperature range up to 750° C. as well as up to 1000° C., and a suitable process for the manufacture of the same, which overcome the hereinafore-mentioned disadvantages of the heretofore-known devices and methods of this general type.

With the foregoing and other objects in view there is provided, in accordance with the invention, a high-temperature gas sensor for the detection of the heat tone of combustible gases, comprising a semiconducting ceramic layer with thermistor properties, the semiconducting ceramic layer being formed of an oxide ceramic semiconducting material having a defined crystalline structure and a thermistor characteristic of high sensitivity.

In accordance with another feature of the invention, there are provided electrical contacts between which the semiconducting ceramic layer is laterally disposed.

In accordance with a further feature of the invention, the semiconducting ceramic layer has a high porosity for achieving greater sensitivity.

With the objects of the invention in view, there is also provided a process for the manufacture of a high-temperature gas sensor for the detection of the heat tone of combustible gases, which comprises sintering a loosely structured layer of powder particles of an oxide semiconductor with both a defined composition and high sinter activity for achieving a required high porosity of a semiconducting ceramic layer with thermistor properties.

In accordance with another mode of the invention, there is provided a process which comprises depositing the loosely structured layer of powder particles of an oxide semiconductor, with a defined composition for achieving a ceramic layer of high porosity, onto a neutral carrier between lateral electrical contacts by electrophoresis from a suspension and sintering.

In accordance with a further mode of the invention, there is provided a process which comprises electrophoretically depositing the sinter-active powder particles with a defined composition between the lateral electrical contacts, and vapor-depositing an electrically conductive $SnO_{2-x}$ intermediate layer partially covering the contacts onto a neutral substrate ceramic.

In accordance with an added mode of the invention, there is provided a process which comprises removing electrical conductivity of the $SnO_{2-x}$ intermediate layer after the electrophoretic deposition of the loosely structured, sinter-active powder particles of defined composition in a subsequent process step in which the oxide ceramic semiconducting layer is thermally fixed to the neutral substrate by sintering, for obtaining an accurate reading of a temperature increase due to the heat tone of an exothermic gas reaction and a decrease in resistance of the oxide ceramic semiconducting layer.

In accordance with an additional mode of the invention, there is provided a process which comprises electrophoretically depositing oxide ceramic powder of the system $Zn_zFe_{z-x}Ni_yMn_{3-x-y}O_4$ onto a neutral ceramic substrate between lateral electrodes and transforming the oxide ceramic powder into a porous semiconducting oxide ceramic layer functioning as a sensor.

In accordance with yet another mode of the invention, there is provided a process which comprises electrophoretically depositing oxide ceramic powder of the system $Fe_xNi_yMn_{3-x-y}O_4$ onto a neutral ceramic substrate between lateral electrodes and transforming the oxide ceramic powder into a porous semiconducting oxide ceramic layer functioning as a sensor.

In accordance with yet a further mode of the invention, there is provided a process which comprises electrophoretically depositing oxide ceramic powder with the composition $MgNiMnO_4$ onto a neutral ceramic substrate between lateral electrodes and transforming the oxide ceramic powder into a porous semiconducting oxide ceramic layer functioning as a sensor.

In accordance with a concomitant mode of the invention, there is provided a process which comprises electrophoretically depositing oxide ceramic powder of the compound $Sr_7Mn_4O_{15}$ onto a neutral ceramic substrate between lateral electrodes and transforming the oxide ceramic powder into a porous semiconducting oxide ceramic layer functioning as a sensor.

Other features which are considered as characteristic for the invention are set forth in the appended claims.

Although the invention is illustrated and described herein as embodied in a high-temperature gas sensor and a process for the manufacture of the same, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

in FIG. 5a, 610° C. in FIG. 5b, 640° C. in FIG. 5c and 670° C. in FIG. 5d;

in FIG. 6a, 610° C. in FIG. 6b, 640° C. in FIG. 6c and 670° C. in FIG. 6d;

in FIG. 7a and 705° C. in FIG. 7b.

DESCRIPTION OF THE PREFERRED EMBODIMENTS

The core idea of the invention lies in the realization of a high temperature measurement sensitivity of a thermistor ceramic with a steep characteristic (large B constants) and high thermal and chemical stability in a thin, porous layer on a neutral carrier. This makes it possible to provide sufficient contact with a gas mixture in which the exothermic reaction occurs so that sensitive detection of combustible components, such as $H_2$, CO, $CH_4$ or other organic, gaseous compounds is possible over the widest possible temperature range.

A particular embodiment of the invention utilizes a thin-film sintered ceramic on the basis of spinels with a composition of either $Zn_zFe_{x-z}NiMn_{2-x}O_4$, $Fe_xNi_yMn_{3-x-y}O_4$ or $MgNiMnO_4$ on an $Al_2O_3$ ceramic as a substrate for applications up to 750° C. or $Sr_7Mn_4O_{15}$ with its own characteristic structure or variants derived therefrom by means of substitution, such as $Sr_{7-x}M_xMn_4O_{15}$ or $Sr_7Mn_{4-y}M_yO_{15}$, on an MgO ceramic substrate for applications up to 1000° C. In this case, M represents a doping agent, which can be yttrium (Y), lanthanum (La) or one of the rare earth elements for the first series of compounds and niobium (Nb), tantalum (Ta) or even titanium (Ti) or scandium (Sc) for the second series of compounds.

The parameters x and y in theory are all greater than 0. However, they can also be equal to 0, where the doping agent is eliminated in the latter case.

With the process according to the invention for the manufacture of a thin-film sintered ceramic, oxalate isomporphous crystals $Fe_xNi_yMn_{3-x-y}(C_2O_4)_3 \cdot 6H_2O$ or $MgNiMn(C_2O_4)_3 \cdot 6H_2O$ are precipitated out of an aqueous acetate solution containing the cations in the proper stoichiometric ratios required for growing the spinels. The crystals then undergo thermal decomposition in a linear heating process to 400° C. and are transformed into a powder in which the spinel structure is already largely present. This process is suitable for the development of a stable suspension for electrophoretic deposition due to its large specific surface.

However, the manufacture of the $Sr_7Mn_4O_{15}$ powder and the compounds derived therefrom by means of substitution specifies the mixing of the components $SrCO_3$ and magnesium oxide, such as $Mn_3O_4$, and possibly a doping agent in proper stoichiometric ratios to form an aqueous slurry, having a solids content after filtering and drying by heating for 12 hours to 1200° C. which is first calcined and subsequently converted to a homogeneous compound by means of grinding, compression densification and renewed heating to 1550° C. The latter must be subsequently ground to achieve a degree of dispersion suitable for electrophoretic deposition of the substance.

According to the invention it is provided that $Al_2O_3$ or MgO ceramic substrate wafers be equipped with two contacts being separated by a gap and applied to the surface by means of the sputtering of platinum or another suitable deposition process using masking. These contacts are then connected by a conductive, transparent layer of $SnO_{2-x}$ being approximately 0.3 µm thick by means of the vaporization of SnO. The manufactured powder is electrophoretically deposited onto this layer in a layer from a suspension prepared from a non-aqueous, sufficiently polar solvent, such as butanol, and 0.25% trichloracetic acid as a dispersing agent (10% relative to the quantity of powder being added) by the application of a voltage of approximately 10 to 100 V. In this case, the voltage is applied and/or the time is used to regulate the layer thickness within a range from 1 µm to approximately 100 µm.

Through the use of sintering at 1000° C., the initially loose powder layer is transformed into a firmly adhering, porous oxide ceramic layer, having electrical parameters which can be set to stable values by means of tempering to 800° C. and not-too-rapid cooling. The initially conductive $SnO_{2-x}$ layer loses its semiconducting properties in this process, so that any interference due to this layer is eliminated and the electrical resistance of the oxide ceramic semiconducting layer is accessible to measurement between the platinum electrodes disposed in a loosely defined geometric configuration.

Figure 1:
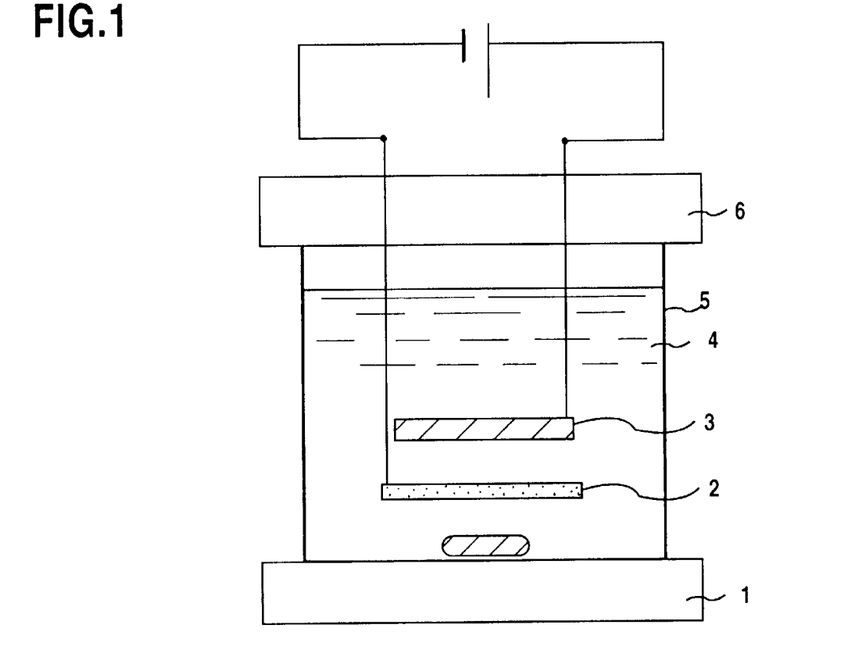
FIG. 1 is a diagrammatic, elevational view of an apparatus for the electrophoretic deposition of oxide ceramic powder between two platinum electrodes on an $SnO_x$ coated $Al_2O_3$ substrate.
Figure 2:
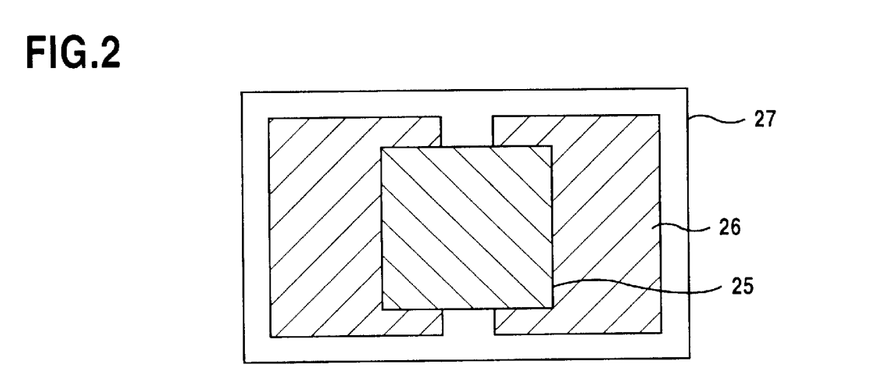
FIG. 2 includes a plan view and an elevational view showing the $Al_2O_3$ substrate wafer with the platinum electrodes applied by means of sputtering, the vapor deposited $SnO_x$ layer and the active layer of oxide ceramic powder applied by means of electrophoretic deposition.
Figure 2A:
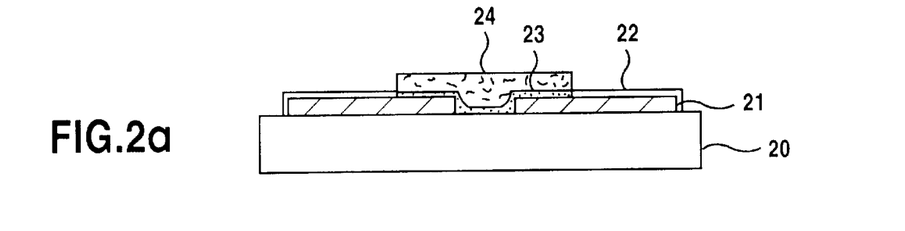

Referring now to the figures of the drawing in detail and first, particularly, to FIG. 1 thereof, there is seen a configuration of an electrophoresis apparatus in which powder particles in a suspension 4 are disposed in a beaker 5. A holding device 6 for electrodes is disposed above the beaker 5 and a magnetic stirrer 1 is disposed below the beaker 5. An $Al_2O_3$ substrate 3 is connected to one electrode as an anode and a cathode 2 is connected to another electrode, in the suspension 4. A negative charge has been applied to the powder particles in the suspension 4 by means of surface absorption, and the powder particles are anodically deposited upward on to a surface of a $SnO_{2-x}$ layer 23, as shown in FIG. 2. It is appropriate in this case to cover that portion of the platinum contacts not coated with $SnO_{2-x}$ with a lacquer which can then be easily removed. Depending on the voltage being applied and the duration of the application, oxide ceramic semiconducting powder can be applied to the substrate wafers in layers with specific thicknesses.

FIG. 2 supplements FIG. 1 and shows both a plan view and an elevational view of an $Al_2O_3$ substrate wafer 27, 20 with 0.1 to 0.15 µm thick platinum contacts 26, 21 that are 5 mm apart and are applied by means of sputtering and an approximately 0.3 µm thick $SnO_{2-x}$ layer 25, 23 (covering the gap and partially covering the platinum contacts) produced by means of vapor deposition and thermal shaping. The oxide ceramic powder is precisely applied onto this layer by means of electrophoretic deposition in layers of between 1 and 100 µm after a lacquer layer covering 22 is applied over the free platinum surface.

Figure 3A:
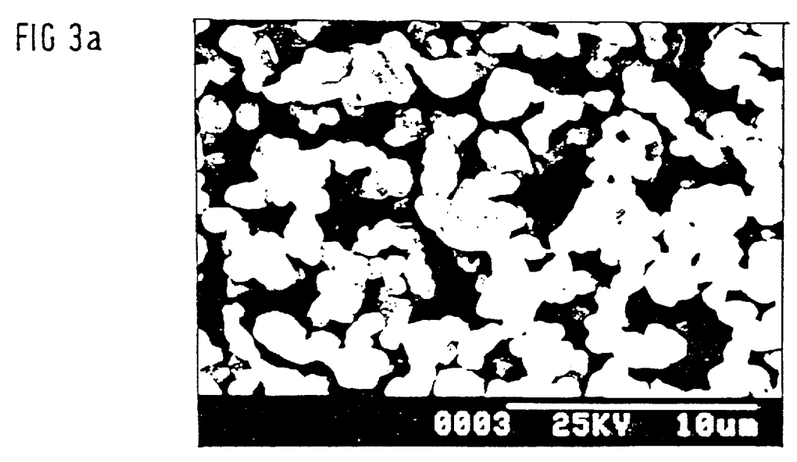
FIGS. 3a and 3b are images produced by a scanning electron microscope showing a large, highly porous surface of the oxide ceramic semiconducting layer, which has been fixed by means of sintering.
Figure 3B:
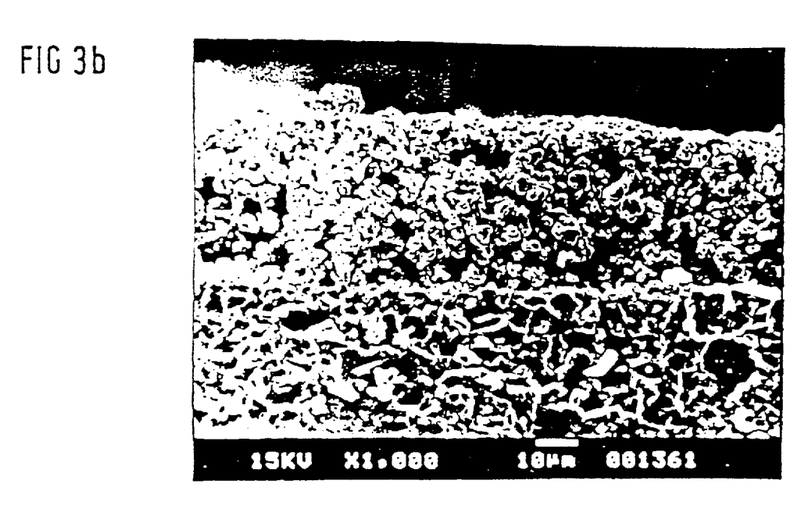

FIGS. 3a and 3b show scanning electron microscope images of the loose structure of the oxide ceramic semiconducting layer after sintering and tempering when viewed from above in FIG. 3a and in a fracture perpendicular to the layer in FIG. 3b. The large surface area provides favorable conditions for local heat transmission between an exothermic gas reaction and the thermistor ceramic with a steep characteristic and also permits the catalytic acceleration of the gas reaction.

Figure 4:
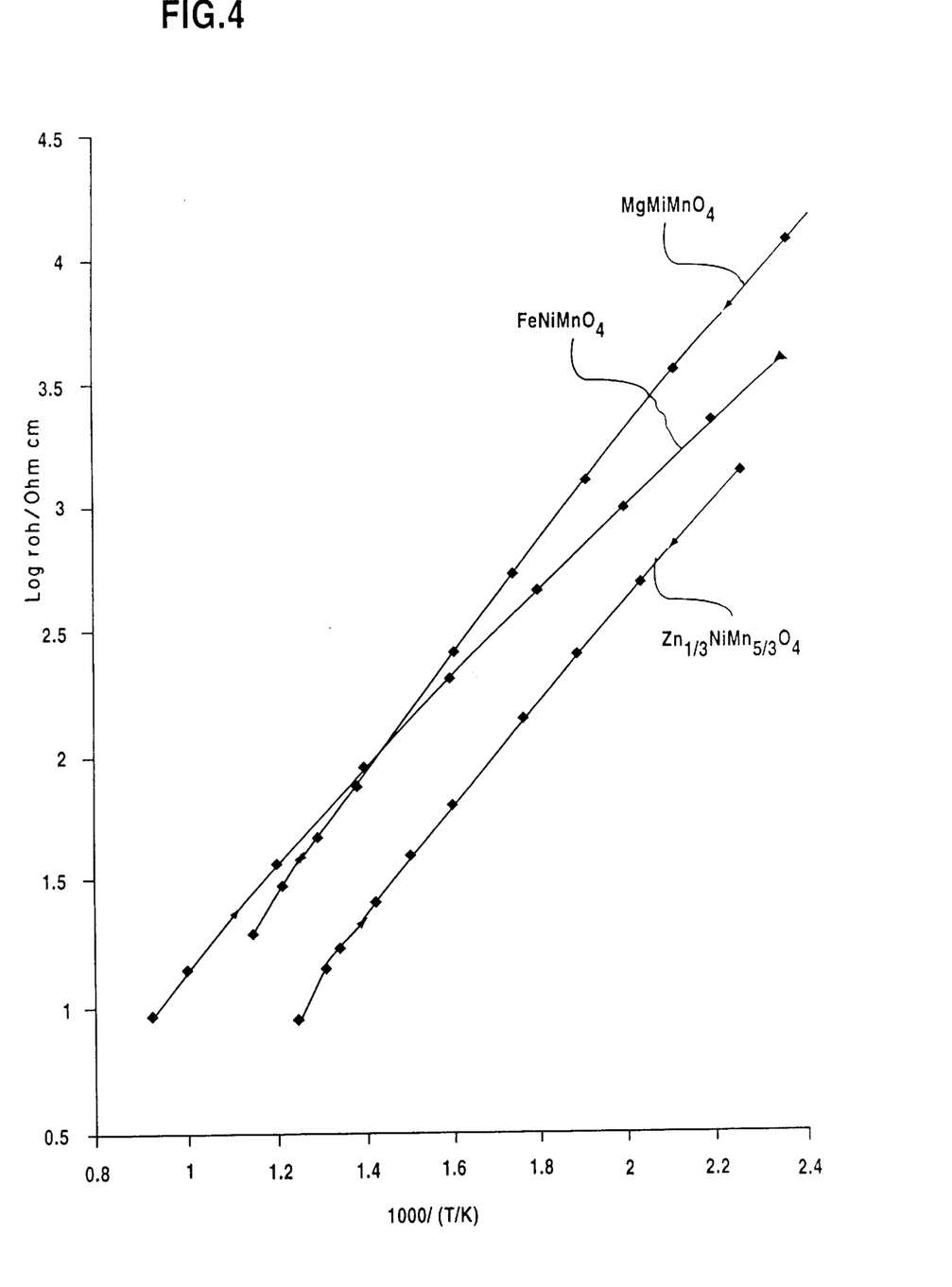
FIG. 4 is a diagram showing non-linear characteristics of the electrical resistance of thin oxide ceramic semiconducting layers, having B constants which loosely correspond with compact probes.

FIG. 4 is a logarithmic representation of the inverse relationship between the specific resistance and the absolute temperature for layers being formed of $Zn_{1/3}NiMn_{5/3}O_4$ (layer thickness 25 µm), $FeNiMnO_4$ (layer thickness 23 µm) and $MgNiMnO_4$ (layer thickness 30 µm). The specific resistance values for 25° C. and the B constants derived from the equation (1) for the temperature range $\theta 1°/\theta 2°$ C. (generally 150°/500° C.) are compiled in Table 1. For comparison, the table also includes values for compact ceramic probes, which were measured in tablet form.

Figure 5A:
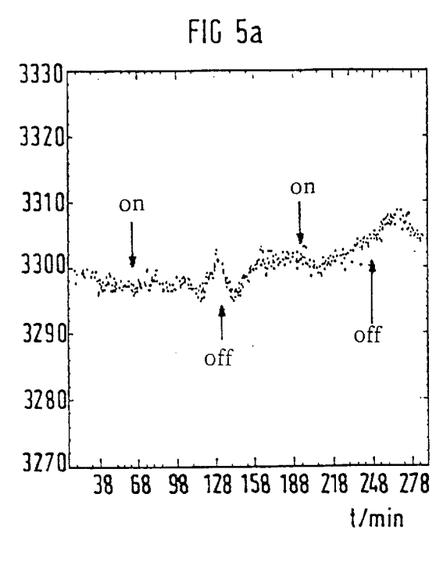
FIGS. 5a–5d are diagrams showing an example of a change in resistance of a $Zn_{1/3}NiMn_{5/3}O_4$ layer as a function of time and an addition or removal of methane (5%) to an $O_2$/argon stream at 580° C.
Figure 5B:
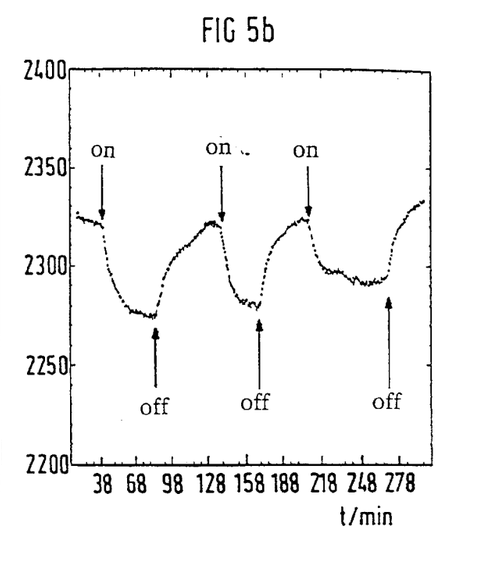
Figure 5C:
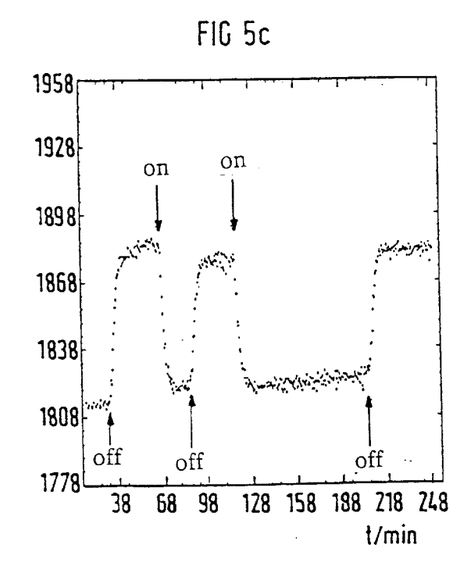
Figure 5D:
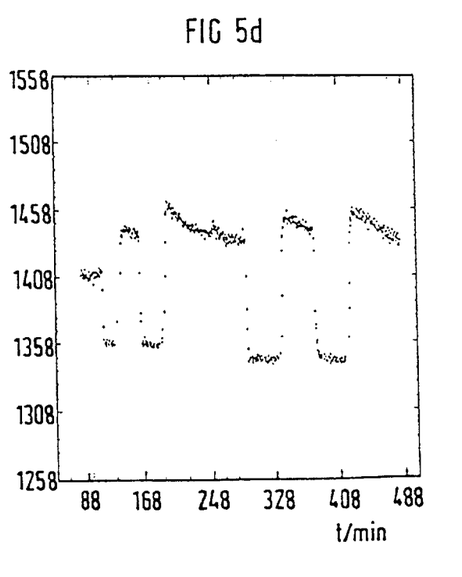
Figure 6A:
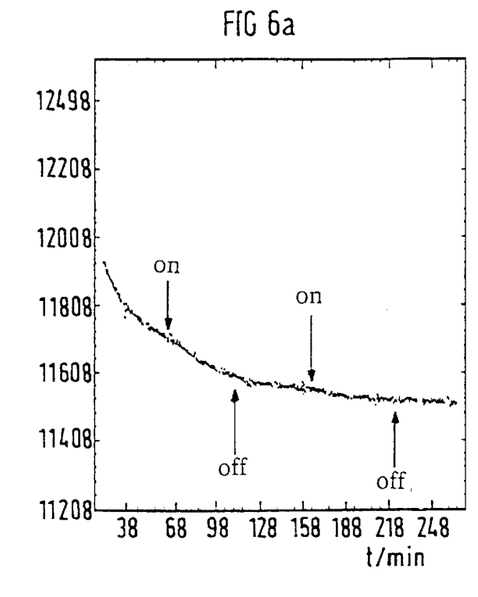
FIGS. 6a–6d are diagrams showing an example of a gas sensor function, a change in resistance of an $FeNiMnO_4$ layer as a function of time and an addition or removal of methane (5%) to an $O_2$/argon stream at 580° C.
Figure 6B:
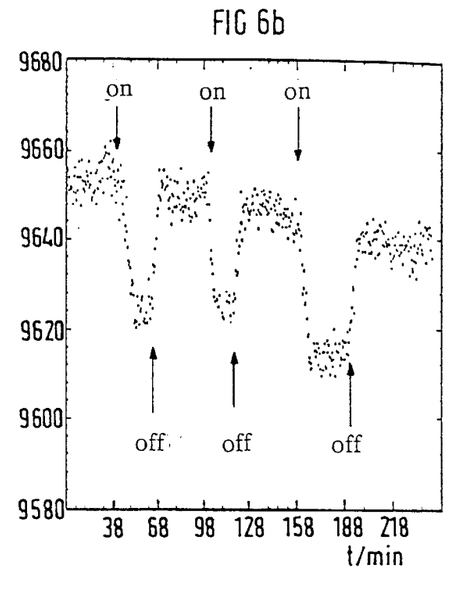
Figure 6C:
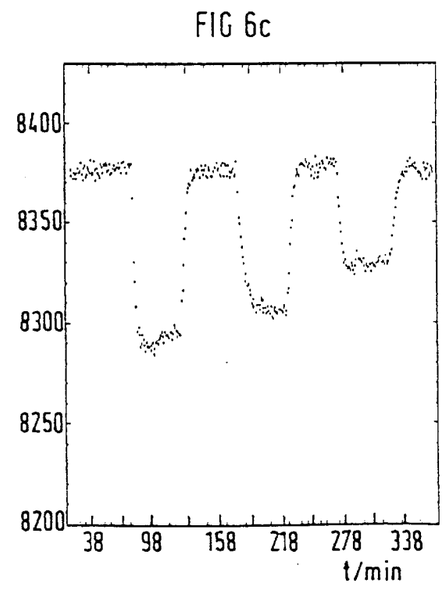
Figure 6D:
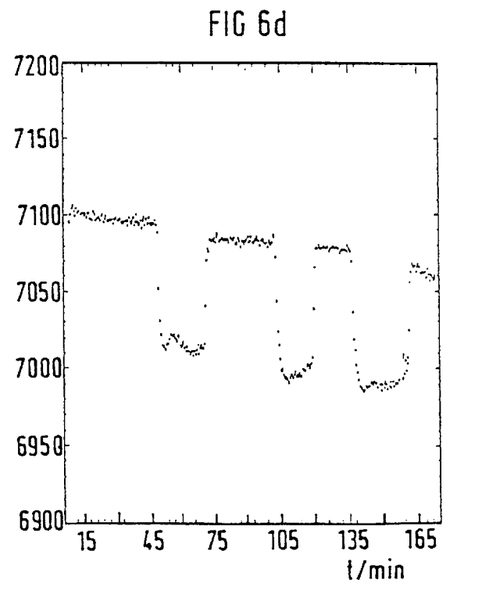

FIGS. 5 and 6 show the detection of methane in an argon stream containing 12% oxygen in addition to 5% methane by means of the heat tone or heat of reaction of the oxidation reaction that begins in the near-surface region of the oxide ceramic semiconducting layer at 610° C. in FIGS. 5b and 6b and, as temperature increases, results in an increasingly greater decrease in resistance at 640° C. in FIGS. 5c and 6c and 670° C. in FIGS. 5d and 6d, which decrease is completely reversible by shutting off the supply of methane. The change in resistance corresponds to a temperature increase of 2.2° C. at 610° C. and 9.6° C. at 670° C. in the case of the $Zn_{1/3}NiMn_{5/3}O_4$ layer, and 0.4° C. at 610° C. and 2.4° C. at 670° C. in the case of the $FeNiMnO_4$ layer. These values, which were calculated according to equation (1), were confirmed by means of independent measurements using a thermoelement.

Figure 7A:
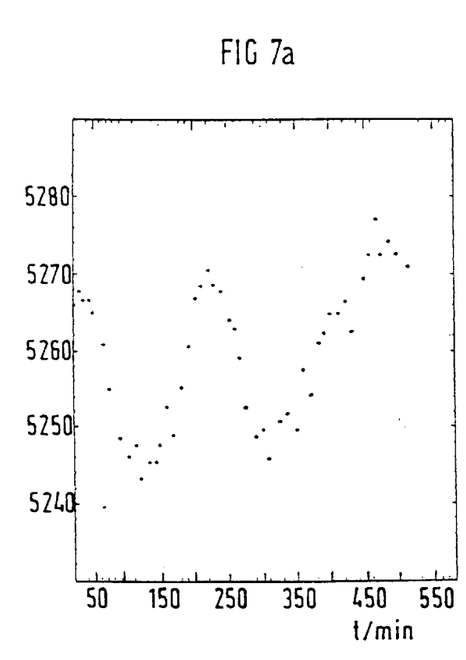
FIGS. 7a–7b are diagrams showing an example of a gas sensor function, a change in resistance of an $MgNiMnO_4$ layer as a function of the time and an addition or removal of methane (5%) to an $O_2$/argon stream at 610° C.
Figure 7B:
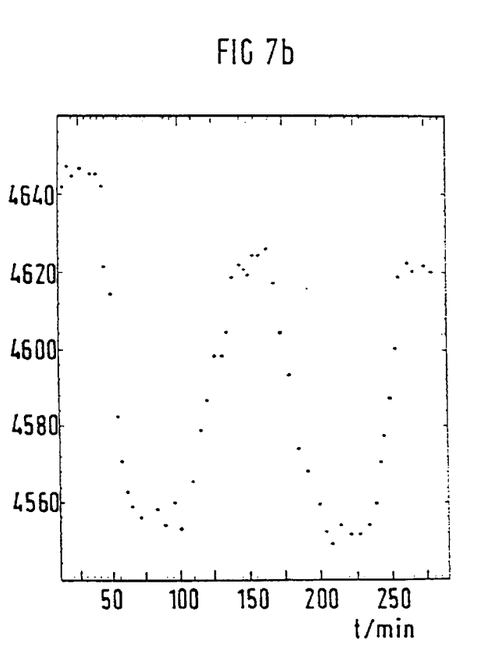

FIG. 7 shows the readings obtained under fully analogous conditions for an $MgNiMnO_4$ layer at 610° C. in FIG. 7a and 705° C. in FIG. 7b.

Figure 8:
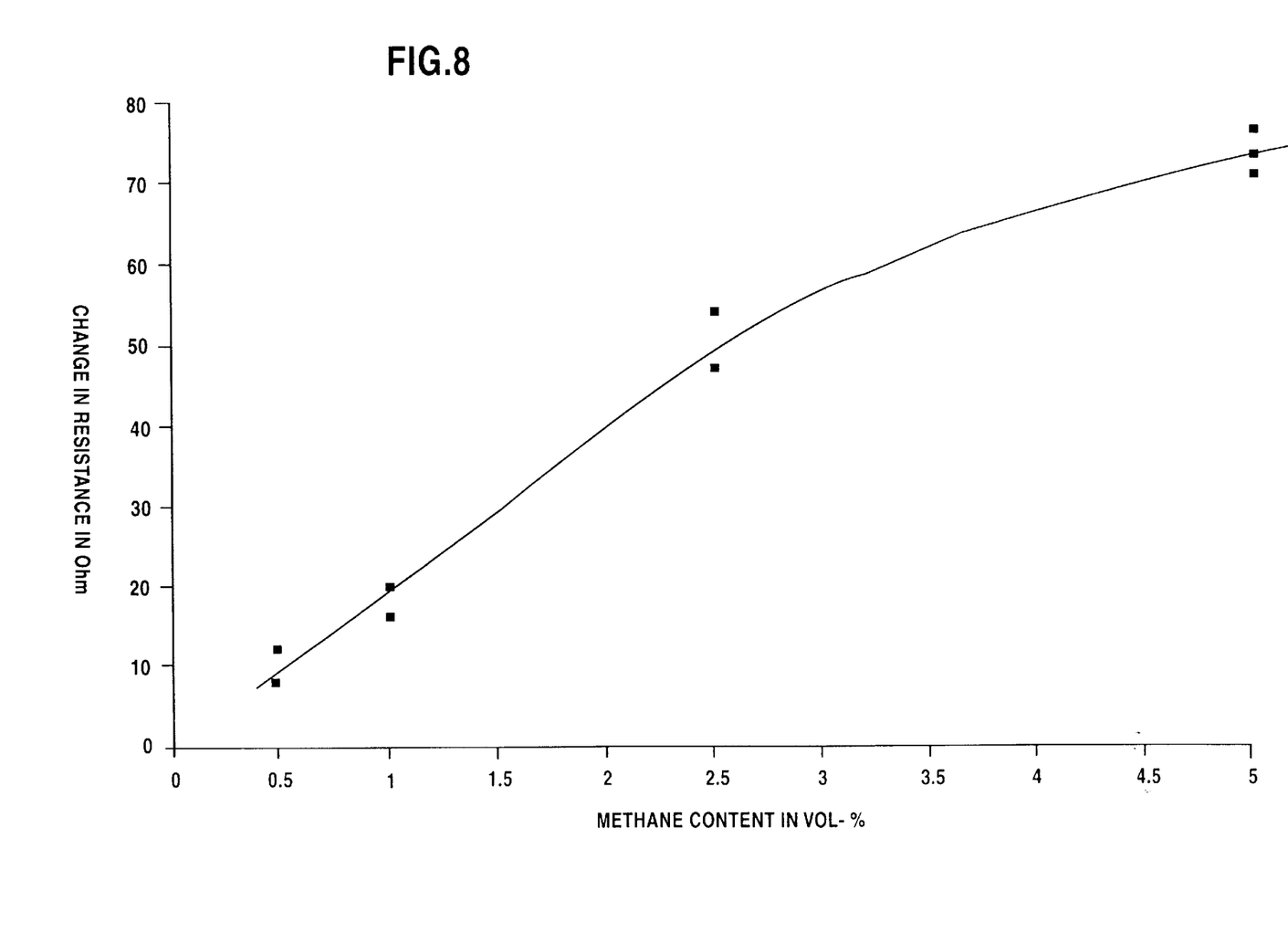
FIG. 8 is a diagram showing an example of a change in resistance at a constant temperature as a function of a $CH_4$ content in air for an $MgNiMnO_4$ layer as is shown in FIGS. 7a and 7b.

FIG. 8 shows the decrease in resistance of the $MgNiMnO_4$ layer pursuant to FIG. 7 at 705° C. as a function of the methane content. The slope of the lines permits estimation of the sensitivity as approximately 150 Ω change in resistance per percent $CH_4$ in the gas mixture. 0.5% $CH_4$ can be detected in a gas mixture by means of the gas sensor layer.

TABLE 1

Electrical parameters of the gas sensor layers and compact ceramic probes of the same composition.

| Substance | $\rho 25°$ C./ Ω cm | $B_{150/500°\ C.}$/K | $\rho 25°$ -C./ Ω cm | B ($\dot{v}_1/\dot{v}_2°$ C./K) |
|---|---|---|---|---|
| $Zn_{1/3}NiMn_{5/3}O_4$ | 2.47 · 10$^5$ | 4775 | 2.78 10$^3$ | 3788 (25/100) |
| $FeNiMnO_4$ | 1.37 · 10$^5$ | 3786 | 5.60 10$^3$ | 3400 25/100 |
| $MgNiMnO_4$ | 2.35 · 10$^6$ | 5265 | 2.06 · 10$^6$ | 4550 (150/500) |
| $Sr_7Mn_4O_{15}$ | — | — | 10$^8$ (100° C.) | 10 000 (350/1100) |

We claim:

1. A gas sensor for detecting a heat tone of combustible gases, comprising:
   a carrier of an $Al_2O_3$ ceramic;
   electrical contacts disposed on said carrier; and
   a semiconducting oxide ceramic layer at least partially covering said electrical contacts, said ceramic layer consisting of a spinel selected from the group consisting of $Zn_zFe_{x-z}NiMn_{2-x}O_4$, $Fe_xNi_yMn_{3-x-y}O_4$, and $MgNiMnO_4$, wherein x and y are greater or equal to zero.

2. The gas sensor according to claim 1, further comprising an electrically nonconducting $SnO_{2-x}$ layer provided between said carrier and said semiconducting oxide ceramic layer.

3. A gas sensor for detecting a heat tone of combustible gases comprising:

a carrier of an MgO ceramic;

electrical contacts disposed on said carrier; and a semiconducting oxide ceramic layer at least partially covering said electrical contacts, said ceramic layer consisting of an SrMn-compound selected from the group consisting of $Sr_7Mn_4O_{15}$, $Sr_{7-x}M_xMn_4O_{15}$, $Sr_7Mn_{4-y}M_yO_{15}$, wherein M is a doping agent, and x and y are greater or equal to zero.

4. The gas sensor according to claim 3, wherein said compound is $Sr_{7-x}M_xMn_4O_{15}$ and said doping agent is selected from the group consisting of yttrium (Y), lanthanum (La) and a rare-earth element.

5. The gas sensor according to claim 3, wherein said compound is $Sr_7Mn_{4-y}M_yO_{15}$ and said doping agent is selected from the group consisting of niobium (Nb), tantalum (Ta), titanium (Ti) and scandium (Sc).

6. The gas sensor according to claim 3, further comprising an electrically nonconducting $SnO_{2-x}$ layer provided between said carrier and said semiconducting oxide ceramic layer, wherein x is greater than zero.

* * * * *